United States Patent
Gavalda Batalla et al.

(10) Patent No.: US 9,789,072 B2
(45) Date of Patent: Oct. 17, 2017

(54) THERAPEUTIC AGENTS FOR USE IN THE PROPYLAXIS AND/OR TREATMENT OF HYPERKINETIC MOVEMENT DISORDERS

(71) Applicant: SOM INNOVATION BIOTECH, S.L., Barcelona (ES)

(72) Inventors: Nuria Gavalda Batalla, Barcelona (ES); Raul Insa Boronat, Barcelona (ES); Nuria Reig Bolano, Barcelona (ES)

(73) Assignee: SOM INNOVATION BIOTECH, S.L., Barcelona (ES)

( * ) Notice: Subject to any disclaimer, the term of this patent is extended or adjusted under 35 U.S.C. 154(b) by 0 days.

(21) Appl. No.: 14/900,028

(22) PCT Filed: Jun. 18, 2014

(86) PCT No.: PCT/EP2014/062786
§ 371 (c)(1),
(2) Date: Dec. 18, 2015

(87) PCT Pub. No.: WO2014/202646
PCT Pub. Date: Dec. 24, 2014

(65) Prior Publication Data
US 2016/0158167 A1 Jun. 9, 2016

(30) Foreign Application Priority Data
Jun. 19, 2013 (EP) .................... 13382230

(51) Int. Cl.
*A61K 31/138* (2006.01)
*A61K 45/06* (2006.01)
*A61K 31/136* (2006.01)

(52) U.S. Cl.
CPC .......... *A61K 31/138* (2013.01); *A61K 31/136* (2013.01); *A61K 45/06* (2013.01)

(58) Field of Classification Search
CPC .................................................. A61K 31/138
See application file for complete search history.

(56) References Cited

U.S. PATENT DOCUMENTS

| | | | | |
|---|---|---|---|---|
| 3,857,891 A | * | 12/1974 | Holmes ................ | C07D 303/22 549/551 |
| 8,183,415 B2 | | 5/2012 | Thiel et al. | |
| 2010/0203168 A1 | | 8/2010 | Zamoyski | |

FOREIGN PATENT DOCUMENTS

| | | |
|---|---|---|
| WO | 2012/117073 A2 | 9/2012 |
| WO | 2012/117076 A2 | 9/2012 |
| WO | 2013/127918 A1 | 9/2013 |

OTHER PUBLICATIONS

Gimeno et al. Clin. Cardiol., 1986, vol. 9, pp. 457-460.*
Chen et al. Clinical Therapeutics, 2012, vol. 34, No. 7, pp. 1487-1504.*
Langlais et al., Database CA [Online]: "Effects of neuropharmacologic agents on a chemically induced hyperkinetic animal model", May 12, 1984, Chemical Abstract Service (2 pages).
Nishimura et al."Involvement of adrenergic and serotonergic nervous mechanisms in a allethrin-induced tremors in mice", May 1, 1984, vol. 9, No. 2, The Journal of Toxicological Sciences, pp. 131-142.
Matsui et al., Database CA [Online]: "Relation of the ataxia in Rolling mouse Nagoya to norepinephrine system", 1983, Chemical Abstracts Services (1 page).
Fischer et al.: "Pharmacologic modulation of central noradrenergic mechanisms and the effect of selected substances on chemically induced seizures: maximal pentylenetetrazole-seizure test (mice)", Feb. 2, 1991, vol. 46, No. 2, Die Phamazie, pp. 151-152.
Lofdahl et al.: "Selectivity of bevantolol hydrochloride, a β 1-adrenoceptor antagonist, in asthmatic patients", 1984, vol. 4, No. 4, Pharmacotherapy, pp. 205-210.
Hirate et al."General Pharmacological Studies of Bevantolol Hydrochloride a Selective BETA-1-Adrenoceptor Blocking Drug", 1992, vol. 44, No. 2, Oyo Yakuri, pp. 167-187.
Zheng G. et al."Vesicular monoamine transporter 2: Role as a novel target for drug development", Nov. 10, 2006, vol. 8, No. 4, AAPS Journal Nov. 10, 2006, p. E682.
Zheng Fang et al."Computational neural network analysis of the affinity of lobeline and tetrabenazine analogs for the vesicular monoamine transporter-2", Jan. 1, 2007, vol. 15, Bioorganic & Medical Chemistry, p. 2975-2992.
Yao et al."Preparation and evaluation of tetrabenazine enantiomers and all eight stereoisomers of dihydrotetrabenazine as VMAT2 inhibitors", Feb. 17, 2011, vol. 46, No. 5, European Journal of Medicinal Chemistry, pp. 1841-1848.
Jankovic et al."Treatment of hyperkinetic movement disorders", Sep. 1, 2009, vol. 8, No. 9, Lancet Neurology, Lancet Publishing Group, GB, p. 844-856.
Sandoval et al."Methylphenidate Redistributes Vesicular Monoamine Transporter-2: Role of Dopamine Receptors", Oct. 1, 2002, vol. 22(19), The Journal of Neuroscience, pp. 8705-8710.
International Search Report for PCT/EP2014/062786, Aug. 19, 2014.

* cited by examiner

Primary Examiner — James D Anderson
(74) Attorney, Agent, or Firm — Merchant & Gould P.C.

(57) ABSTRACT

(RS)-[2-(3,4-dimethoxyphenyl)ethyl][2-hydroxy-3-(3-methylphenoxy)propyl]amine having the formula (IA), or a pharmaceutically acceptable salt thereof for the formulation of a pharmaceutical composition is useful for the prophylaxis and/or the treatment of hyperkinetic movement disorders associated with Huntington's disease, Wilson's disease, Tourette syndrome, restless leg syndrome, and tardive dyskinesia.

17 Claims, No Drawings

THERAPEUTIC AGENTS FOR USE IN THE PROPYLAXIS AND/OR TREATMENT OF HYPERKINETIC MOVEMENT DISORDERS

This application is a National Stage Application of PCT/EP2014/062786, filed 18 Jun. 2014, which claims benefit of Ser. No. 13/382,230.4, filed 19 Jun. 2013 in the European Patent Office and which applications are incorporated herein by reference. To the extent appropriate, a claim of priority is made to each of the above disclosed applications.

This invention relates to a second medical indication of known therapeutic agents. Particularly, this invention relates to a therapeutic agent having two aromatic carbocyclic rings connected by a ($C_4$-$C_7$)alkyl chain comprising at least one nitrogen or oxygen atom for use in the prophylaxis and/or treatment of hyperkinetic movement disorders.

BACKGROUND ART

Movement disorders are a group of central nervous system conditions and/or diseases in which the control of movement is altered with relative preservation of strength, muscle bulk, and mechanical range of motion. They include those diseases which either involve an excess of movement or with a paucity of voluntary and automatic movements. Thus, the movement disorders can be divided into hyperkinesias (excessive movements), dyskinesias (unnatural movements), hypokinesias (paucity of movements), and abnormal involuntary movements.

Hyperkinetic movement disorders (also known as hyperkinesia) imply an increase in muscular activity that can result in excessive movements, either normal, or abnormal movements, or a combination of both.

The hyperkinetic movements can be defined as a wide array of movement disorders characterized by excessive repetitive or sporadic involuntary movements. The most frequently hyperkinetic symptoms are, among others, ataxia, athetosis, chorea, dystonia, ballismus, hemifacial spasm, myoclonus, stereotypes, tardive dystonia, tics, and tremors. The movements can be rhythmic, discrete, repeated, and/or random. The specific pathophysiology of these disorders is diverse although many hyperkinetic movements are the result of improper regulation of the basal ganglia-thalamo-cortical circuitry.

Each disorder can feature one or more hyperkinetic movements as prominent symptoms, for example in disorders like Huntington's disease, tardive dyskinesia and Tourette syndrome.

Huntington's disease (HD) is a dominantly inherited neurodegenerative genetic disorder that affects muscle coordination and leads to cognitive decline and psychiatric problems. HD is due to mutations in the gene encoding for huntingtin, and it is the most common genetic cause of abnormal involuntary writhing movements called chorea, which is why the disease used to be called Huntington's chorea. Thus, the term "Huntington's disease" and "Huntington's chorea" have the same meaning and are used interchangeable. The most prominent early effects in HD are in a part of the basal ganglia called the neostriatum, which is composed of the caudate nucleus and putamen. Symptoms of the disease can vary between individuals, but usually progress predictably. The earliest symptoms are often subtle problems with mood or cognition, followed by a general lack of coordination and an unsteady gait. In advanced stages of the disease, uncoordinated, jerky body movements become more apparent, along with a decline in mental abilities, as well as behavioural and psychiatric problems. Physical abilities are gradually impeded until coordinated movement becomes very difficult, and mental abilities generally decline into dementia. Although the genetic basis of the pathology is well known there is not yet a cure for HD. The pharmacological and non-pharmacological treatments disclosed in the state of the art are focused in minimizing the symptoms of the disease, mainly in relieving the hyperkinetic movements associated to HD.

Tourette syndrome (TS) is a neurologic disorder manifested by motor and vocal or phonic tics usually starting during childhood and often accompanied by some comorbid behavioural problems such as obsessive-compulsive disorder or attention-deficit hyperactivity disorder. Tics are defined as involuntary, sudden, rapid, recurrent, non-rhythmic movement (motor tics) and vocalisations (vocal or phonic tics). The cause of TS is yet unknown, but the disorder appears to be inherited in the majority of patients, as shown by early family studies. Little is known about the exact brain mechanisms associated with tic development and expression, although preliminary evidence from neurochemical and neuroimaging investigations suggests a primary role for dysfunction of the dopaminergic pathways within the cortico-striato-cortico-frontal circuitry. Treatment of TS includes both pharmacotherapy and cognitive behavioural treatment.

Tardive dyskinesia (TD) is a disorder characterized by involuntary, repetitive body movements and is the result of treatment with dopamine receptor-blocking agents. The principal site affected by classic TD is the face, particularly around the mouth, typically called oral-buccal-facial dyskinesia. The limbs and trunk are affected less often than the mouth. The TD syndromes tend to appear late in the course of treatment, hence the term tardive. The symptoms can occur when the patient is taking these drugs or within a period of time after stopping the treatment.

The restless legs syndrome (RLS) is characterized by a deep, ill-defined discomfort or dysesthesia in the legs, which arises during prolonged rest, or when the patient is drowsy and trying to fall asleep, especially at night. The most commonly associated medical condition is iron deficiency although there is also evidence to suggest that the disorder in many if not most patients is transmitted as an autosomal dominant trait.

Wilson's disease is an inborn error of copper metabolism manifest as hepatic cirrhosis and basal ganglia damage. The condition is due to mutations in the Wilson disease protein (ATP7B) gene and the initial manifestations of the illness are neurologic in about 40% of patients. The pathologic abnormalities in the brain are primarily in the basal ganglia, with cavitary necrosis of the putamen and caudate, associated with neuronal loss, axonal degeneration and astrocytosis. In addition, there is cortical atrophy.

One of the pharmacological symptomatic treatments of the hyperkinetic movement disorders disclosed in the state of the art is based on the administration of an inhibitor of the vesicular monoamine transporter 2 (VMAT2). In the striatum, VMAT2 mainly transports dopamine from cellular cytosol into synaptic vesicles from dopaminergic neurons, protecting it from auto-oxidization in the presence of oxygen radicals. Thus, inhibition of VMAT2 reduces the uptake of dopamine into the synaptic vesicles resulting in an overall reduction in total dopamine.

In particular, tetrabenazine ((SS,RR)-3-isobutyl-9,10-dimethoxy-1,3,4,6,7,11b-hexahydro-pyrido[2,1-a]isoquinolin-2-one) is a selective inhibitor of the monoamine transporter VMAT2 which blocks the transport of dopamine to the presynaptic neuronal vesicles, impairing its release to the synaptic cleft. Tetrabenazine is a reversible inhibitor of VMAT2, and the approved drug for the symptomatic treatment of chorea associated to Huntington's disease, tardive dyskinea, and Tourette syndrome, as well as for symptoms like hemiballismus.

Unfortunately, tetrabenazine has a poor and variable bioavailability, being also extensively metabolised by first-pass metabolism. Additionally, tetrabenazine has a black-box warning because of an increase in depression and suicidality, as well as the potential to cause Parkinsonism and Neuroleptic Malignant Syndrome.

Despite all the research efforts invested in the past, the prophylaxis and/or treatment of hyperkinetic movement disorders is far from being satisfactory. Therefore, there is a high unmet need for a safe and effective treatment for those disorders.

SUMMARY OF THE INVENTION

Inventors have surprisingly found that compounds of formula (I) allow the prevention or the amelioration of hyperkinetic movement disorders. As it is shown in the examples below, the compounds of the invention have been identified as VMAT2 inhibitors, exhibiting similar VMAT2 inhibition values compared with tetrabenazine, the marketed active ingredient for the treatment of the above mentioned disorders. Thus, the compounds of formula (I) have an effective activity in the prophylaxis and/or treatment of hyperkinetic movement disorders.

The embodiments of the invention can be applied to all symptoms related to unwanted and excess movement associated to hyperkinesias. The present invention also engages from initial to advanced stages of the evolution of hyperkinesias.

Accordingly, the present invention relates to compounds of formula (I) or their pharmaceutically acceptable salts

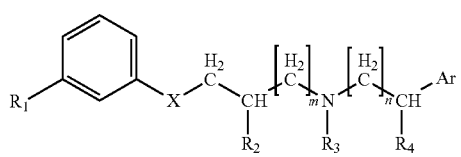

(I)

for use in the prophylaxis and/or treatment of some hyperkinetic movement disorders; wherein: $R_1$ is selected from the group consisting of H, $CH_3$, and $CF_3$; $R_2$ is selected from the group consisting of H, OH, and $CH_3$; $R_3$ is H or —$CH_2CH_2Cl$; $R_4$ is H or $CH_3$; Ar is selected from the group consisting of 1-naphtyl, phenyl, and 3,4-dimethoxyphenyl; X is $CH_2$ or O; and m, and n are integers selected from 0 and 1; with the proviso that: $R_1$ is $CH_3$, $R_2$ is OH, $R_3$ is H, $R_4$ is H, Ar is 3,4-dimethoxyphenyl, X is O, m is 1, and n is 1; or $R_1$ is $CF_3$, $R_2$ is H, $R_3$ is H, $R_4$ is $CH_3$, Ar is 1-naphtyl, X is $CH_2$, m is 0, and n is 0; or $R_1$ is H, $R_2$ is $CH_3$, $R_3$ is —$CH_2CH_2Cl$, $R_4$ is H, Ar is phenyl, X is O, m is 0, and n is 0.

The compounds of formula (I) are: bevantolol, cinacalcet, and phenoxybenzamine.

Bevantolol is the name commonly used for (RS)-[2-(3,4-dimethoxyphenyl)ethyl][2-hydroxy-3-(3-methylphenoxy)propyl]amine having CAS RN 59170-23-9 of formula (IA)

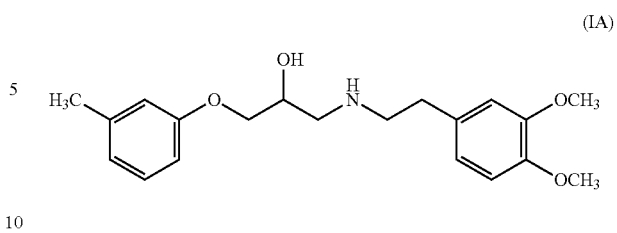

(IA)

It is a beta-1 adrenoreceptor antagonist that has been shown to also have both agonist and antagonist effects on alpha adrenoreceptor. It is used for the treatment of angina pectoris and hypertension.

Cinacalcet is the name commonly used for (R)—N-[1-(1-naphthyl)ethyl]-3-[3-(trifluoromethyl)phenyl]propan-1-amine) having CAS RN 226256-56-0 of formula (IB).

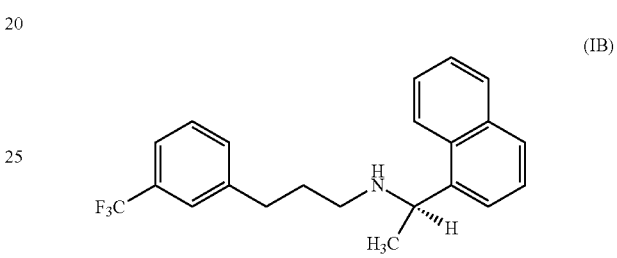

(IB)

It is an active ingredient that acts as a calcimimetic agent by allosteric activation of the calcium-sensing receptor expressed in the surface of the chief cell of the parathyroid gland. It has been safely administered to humans for the treatment of secondary hyperparathyroidism and for the parathyroid carcinoma.

WO2012117073 discloses a combined therapy for the treatment of neurological disorders which comprises a first active ingredient selected from a first list and at least a second active ingredient selected from a second list, wherein the second list includes among others cinacalcet. In particular, it is only disclosed the effect on the cognitive performance on Alzheimer's disease animal models.

Phenoxybenzamine is the name commonly used for (RS)—N-benzil-N-(2-chloroetyl)-1-phenoxy-propan-2-amine having CAS RN 59-96-1 of formula (IC)

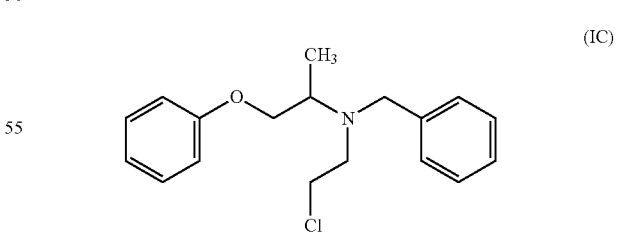

(IC)

It is a non-selective, irreversible alpha adrenoreceptor antagonist that has been indicated to control episodes of hypertension and sweating in the treatment of pheochromocytoma.

In particular, the present invention relates to a compound of formula (IA) or a pharmaceutically acceptable salt thereof

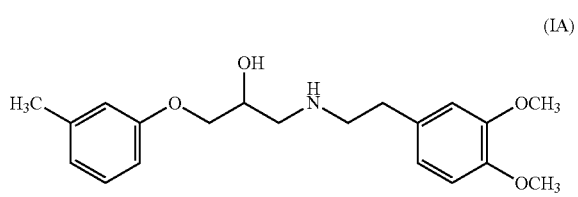 [SMILES: COc1ccc(CCNCC(O)COc2cccc(C)c2)cc1OC]

(IA)

for use in the prophylaxis and/or treatment of a hyperkinetic movement disorder associated with Huntington's disease, Wilson's disease, Tourette syndrome, restless leg syndrome, and tardive dyskinesia.

Consequently, none of the compounds of formula (I) have already been disclosed or suggested for the prophylaxis and/or treatment of hyperkinetic movement disorders.

DETAILED DESCRIPTION OF PARTICULAR EMBODIMENTS

As mentioned above, the invention relates to a compound of formula (I) or a pharmaceutically acceptable salt thereof for use in the prophylaxis and/or treatment of hyperkinetic movement disorders. This aspect could be formulated as the use of a compound of formula (I) or a pharmaceutically acceptable salt thereof for the preparation of a medicament for the prophylactic and/or therapeutic treatment of hyperkinetic movement disorders in a mammal, including a human. This aspect could also be formulated as a method for the treatment and/or prophylaxis of a mammal, including a human, suffering from or being susceptible of suffering from hyperkinetic movement disorders, the method comprising the administration to said patient of a therapeutically effective amount of a compound of formula (I) or a pharmaceutically acceptable salt thereof, together with pharmaceutically acceptable excipients or carriers.

In a particular embodiment, a compound of formula (IA) or a pharmaceutically acceptable salt thereof

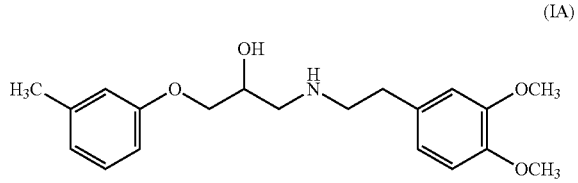 [SMILES: COc1ccc(CCNCC(O)COc2cccc(C)c2)cc1OC]

(IA)

for use in the prophylaxis and/or treatment of a hyperkinetic movement disorder associated with Huntington's disease, tardive dyskinesia, Wilson's disease, Tourette syndrome, and restless leg syndrome.

In an embodiment, a compound of formula (IA) or a pharmaceutically acceptable salt thereof for use in the prophylaxis and/or treatment of a hyperkinetic movement disorder associated with Huntington's disease, Wilson's disease, Tourette syndrome, and restless leg syndrome.

In an embodiment of the invention, the compounds of formula (I) or their pharmaceutically acceptable salt thereof can be used in the treatment of hyperkinetic movement disorders. In a particular embodiment, the compound of formula (IA) or their pharmaceutically acceptable salt thereof, for use in the treatment of the hyperkinetic movement disorder associated with Huntington's disease, tardive dyskinesia, Wilson's disease, Tourette syndrome, and restless leg syndrome. In an embodiment, for use in the treatment of the hyperkinetic movement disorder associated with Huntington's disease, Wilson's disease, Tourette syndrome, and restless leg syndrome.

Any pharmaceutically acceptable salt of a compound of formula (I) can be used for the purposes of the invention. The expression "pharmaceutically acceptable salt" refers to salts prepared from pharmaceutically acceptable non-toxic acids which are, within the scope of medical judgement, suitable for use in contact with the tissues of humans and animals without excessive toxicity, irritation, allergic response, or other problem or complication, commensurate with a reasonable benefit/risk ratio.

Some compounds of the invention can have chiral centres that can give rise to various stereoisomers. As used herein, the term "stereoisomer" refers to all isomers of individual compounds that differ only in the orientation of their atoms in space. The term stereoisomer includes mirror image isomers (enantiomers), and mixtures of mirror image isomers (racemates, racemic mixtures). The present invention relates to each of these stereoisomers and also mixtures thereof. Enantiomers can be separated by conventional techniques such as chromatography or fractional crystallization. Optical isomers can be resolved by conventional techniques of optical resolution to give optically pure isomers. This resolution can be carried out on any chiral synthetic intermediates or on compounds of the invention. Optically pure isomers can also be individually obtained using enantiospecific synthesis.

The expression "pharmaceutically acceptable excipients or carriers" refers to pharmaceutically acceptable materials, compositions or vehicles. Each component must be pharmaceutically acceptable in the sense of being compatible with the other ingredients of the pharmaceutical composition. It must also be suitable for use in contact with the tissue or organ of humans and animals without excessive toxicity, irritation, allergic response, immunogenicity or other problems or complications commensurate with a reasonable benefit/risk ratio.

In a preferred embodiment, the compound for use of the present invention is that wherein $R_1$ is $CH_3$, $R_2$ is OH, $R_3$ is H, $R_4$ is H, Ar is 3,4-dimethoxyphenyl, X is O, m is 1, and n is 1. This compound is the known compound bevantolol of formula (IA).

In another preferred embodiment, the compound for use of the present invention is that wherein $R_1$ is $CF_3$, $R_2$ is OH, $R_3$ is H, $R_4$ is H, Ar is 3,4-dimethoxyphenyl, X is O, m is 1, and n is 1. This compound is the known compound cinacalcet of formula (IB).

In another preferred embodiment, the compound for use of the present invention is that wherein $R_1$ is H, $R_2$ is $CH_3$, $R_3$ is —$CH_2CH_2Cl$, $R_4$ is H, Ar is phenyl, X is O, m is 0, and n is 0. This compound is the known compound phenoxybenzamine of formula (IC).

The compounds of the invention are used in the prophylaxis and/or treatment of hyperkinetic movement disorders. Examples of hyperkinetic movements include abdominal dyskinesias, akathisic movements, asynergia, ataxia, athetosis, ballism, chorea, dysmetria, dystonia, hemifacial spasm, hyperekplexia, hypnogenic dyskinesias, jumpy stumps, moving toes and/or fingers, myoclonus, myokymia, myorhythmia, paroxysmal dyskinesias, tics, and tremor. In an embodiment of the invention, the hyperkinetic movement disorders are selected from the group consisting of chorea, dystonia, myoclonus, stereotypy, tics, ballism and tremors. In a preferred embodiment, the hyperkinetic movement disorder is selected from tics, ballism, dystonia and chorea.

In a preferred embodiment, the hyperkinetic movement disorder is chorea. The term chorea as used herein refers to a hyperkinetic movement disorder that consists of involuntary, continual, abrupt, rapid, brief, unsustained, irregular movements that flow randomly from one body part to another. Chorea may be a manifestation of a primary neurologic genetic disorder, such as Huntington's disease, or it may occur as a neurologic complication of other disorders such as systemic disorders, toxic disorders, and/or a pharmacological treatment such as the treatment with dopamine receptors antagonists, causing, for example, tardive chorea and withdrawal emergent syndrome.

In another preferred embodiment, the hyperkinetic movement disorder is ballism. It refers to a rare movement disorder that consists of flailing, ballistic, and undesired movements of the limbs. The involuntary movement usually affects only one side of the body; the term hemiballism is used to describe unilateral ballism. Damage to the subthalamic nucleus and the pallido-subthalamic pathways are the main causes associated with ballism.

In another preferred embodiment the hyperkinetic movement disorder is tic. It refers to relatively brief, abrupt and intermittent movement (motor tics) or sounds (vocal or phonic tics). They vary in frequency and intensity and often change distribution. Increased activity in the right caudate nucleus, right frontal cortex and other cortical areas of the brain has been related to the appearance of tics.

In another preferred embodiment the hyperkinetic movement disorder is dystonia. It refers to involuntary movements and extended muscle contractions. The dystonic patient has twisting body movements, tremor and unusual or awkward postures. For some patients the whole body may be involved in the movements, while for others only certain parts of the body are affected. Dystonia can be classified by age of onset, by body parts(s) affected and by etiology (primary or secondary). Decreased neurotransmitter production in the basal ganglia is most likely associated with primary dystonia symptoms. However, there are also a number of dystonias that have a genetic origin.

The hyperkinetic movements as mentioned above can be associated with several diseases or disorders. Examples of diseases that feature one or more hyperkinetic movements include, Huntington's disease, Huntington's disease-like diseases (HDL1, HDL2 and HDL3), Sydenham chorea, benign hereditary chorea, neuroacanthocytosis, neurodegeneration with brain iron accumulation (NBIA), athetosis, Wilson's disease, Tourette syndrome, restless leg syndrome, tardive dyskinesia, Friedreich ataxia, spinocerebellar ataxia, multiple system atrophy, dentatorubral-pallidoluysian atrophy, ataxia with oculomotor apraxia (types 1 and 2), ataxia telangiectasia, focal dystonias, idiopathic dystonias such as Oppenheim dystonia and torticollis, dystonia-plus syndromes, secondary dystonias, Duchenne muscular dystrophy, Down syndrome, Parkinson's disease, and progressive supranuclear palsy.

In an embodiment of the invention, suitable diseases that feature one or more of hyperkinetic movements for the present invention are selected from the group consisting of Huntington's disease, Wilson's disease, Tourette syndrome, tardive dyskinesia and restless leg syndrome. In an embodiment, the hyperkinetic movements for the present invention are selected from the group consisting of Huntington's disease, Wilson's disease, Tourette syndrome and restless leg syndrome. In a preferred embodiment, the disease is selected from Huntington's disease, Tourette syndrome, and tardive dyskinesia.

In a preferred embodiment, the compound of formula (I) for use in the prophylaxis and/or treatment of chorea associated to Huntington's disease, Tourette syndrome, and tardive dyskinesia. Particularly, the compound of formula (I) for use in the prophylaxis and/or treatment of chorea associated to Huntington's disease. In a particular embodiment, the compound of formula (IA) for use in the prophylaxis and/or treatment of chorea associated to Huntington's disease, Tourette syndrome, and tardive dyskinesia. Particularly, in the prophylaxis and/or treatment of chorea associated to Huntington's disease.

In another preferred embodiment, the compound of formula (I) for use in the prophylaxis and/or treatment of tics associated to Tourette syndrome and tardive dyskinesia.

Effective quantities of a compound of formula (I), particularly the compound of formula (IA) or pharmaceutically acceptable salts thereof are preferably administered to a patient in need of such treatment according to usual routes of administration and formulated in usual pharmaceutical compositions, comprising an effective amount of the active ingredient and a suitable pharmaceutically acceptable carrier, and dosage forms according to methods known in the art.

The expression "therapeutically effective amount" as used herein, refers to the amount of the active ingredient that, when administered, is sufficient to prevent development of, or alleviate to some extent, one or more of the symptoms of the disease which is addressed. The particular dose of compound administered according to this invention will be determined by the particular circumstances surrounding the case, including the compound administered, the route of administration, the particular condition being treated, and similar considerations. In particular, the term "therapeutically effective amount of a compound of formula (I)" as used herein, refers to the amount of the compound of formula (I) that is sufficient to prevent or alleviate to some extent one or more of the hyperkinetic movement. Particularly, the amount of the compound of formula (I) that is sufficient to prevent or alleviate to some extent one or more of the hyperkinetic movement associated to HD. In particular, the term "therapeutically effective amount of a compound of formula (IA)" as used herein refers to the amount of the compound of formula (IA) that is sufficient to prevent or alleviate to some extent one or more of the hyperkinetic movement associated with Huntington's disease, Wilson's disease, Tourette syndrome, tardive dyskinesia and restless leg syndrome; Particularly, Huntington's disease, Wilson's disease, Tourette syndrome, and restless leg syndrome. In an embodiment, the amount of the compound of formula (I), particularly (IA) that is sufficient to prevent or alleviate to some extent one or more of the hyperkinetic movement associated to Huntington's disease, Tourette syndrome and tardive dyskinesia.

The individual dosage as well as the daily dosage varies depending upon the type and severity of the hyperkinetic movement to be treated, and the specific patient's response to the medication. Therefore, the exact individual dosage will be determined according to standard medical principles under the direction of a physician.

The effective daily dose of a compound of formula (I) for use in the treatment of hyperkinetic movement disorders is comprised from 1 to 10000 mg/day. In a particular embodiment, when the compound of formula (I) is the compound of formula (IA), the effective daily dose for use in the treatment of hyperkinetic movement disorders is comprised from 1 to 6000 mg/day; preferably from 1 to 3000 mg/day; more preferably from 1 to 600 mg/day. In another particular embodiment, when the compound of formula (I) is the compound of formula (IB), the effective daily dose for use in the treatment of hyperkinetic movement disorders is comprised from 1 to 4000 mg/day; preferably from 1 to 400 mg/day. In another particular embodiment, when the compound of formula (I) is the compound of formula (IC), the effective daily dose for use in the treatment of hyperkinetic movement disorders is comprised from 1 to 2000 mg/day; preferably from 1 to 200 mg/day.

The compound of formula (I) or a pharmaceutically acceptable salt thereof can be used either alone or in combination therapy with another compound of formula (I) or with other therapeutic agents. In a particular embodiment, the compound of formula (IA) or a pharmaceutically acceptable salt thereof can be used either alone or in combination therapy with a compound of formula (IB), a compound of formula (IC) or with other therapeutic agents.

In an embodiment of the invention, the compound of formula (I) for use in the prophylaxis and/or treatment of a hyperkinetic movement disorder, wherein said prophylaxis or treatment comprises administering as a unique active ingredient the compound of formula (I). In a particular embodiment, the compound of formula (IA) for use in the prophylaxis and/or treatment of a hyperkinetic movement disorder associated with Huntington's disease, Wilson's disease, Tourette syndrome, tardive dyskinesia and restless leg syndrome, wherein said prophylaxis or treatment comprises administering as a unique active ingredient the compound of formula (IA); particularly Huntington's disease, Wilson's disease, Tourette syndrome, and restless leg syndrome.

In another embodiment of the invention, the compound of formula (I) for use in the prophylaxis and/or treatment of a hyperkinetic movement disorder, wherein said prophylaxis or treatment comprises administering the compound of formula (I) in combination therapy with an additional therapeutic agent selected from the group consisting of another compound of formula (I), a neuroleptic agent, an antiglutamatergic agent, a dopamine depleting agent, an acetyl cholinesterase inhibitor, and mixture thereof. In a preferred embodiment, the additional therapeutic agent is selected from the group consisting of another compound of formula (I), amantadine, riluzole, tetrabenazine, reserpine, and donepezil; preferably, the additional therapeutic agent is tetrabenazine.

In a particular embodiment, the compound of formula (IA) for use in the prophylaxis or treatment comprises administering the compound of formula (IA) in combination therapy with an additional therapeutic agent selected from the group consisting of a compound of formula (IB), a compound of formula (IC), a neuroleptic agent, an antiglutamatergic agent, a dopamine depleting agent, an acetyl cholinesterase inhibitor, and mixture thereof;

wherein:
the compound of formula (IB) is

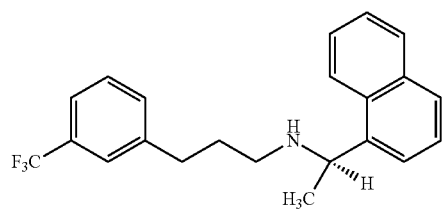

(IB)

and the compound of formula (IC) is

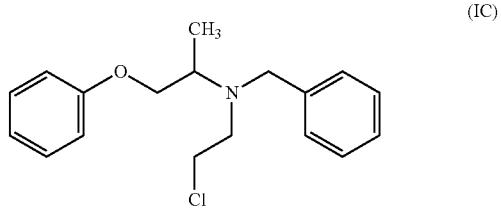 [SMILES: CC(COc1ccccc1)N(CCCl)Cc1ccccc1]

(IC)

As will be apparent to the skilled in the art, the combination of the invention comprising a compound of formula (I) with an additional therapeutic agent is effective not only when the active ingredients are used in a single composition, but also when used in two different compositions, either administered simultaneously, sequentially or separately after a certain period of time. Furthermore, the skilled in the art will understand that the compound of formula (I), particularly compound of formula (IA), can be prescribed to be used together with the other active ingredient in a combination therapy in order to prevent and/or treat a hyperkinetic movement disorder.

In a particular embodiment, the combination therapy comprises administering to a subject simultaneously, sequentially or separately the compound of formula (I) and the additional therapeutic agent. Alternatively, the combination therapy comprises administering to a subject the compound of formula (I) and the additional therapeutic agent in a single composition.

In a particular embodiment, the combination therapy comprises administering to a subject simultaneously, sequentially or separately the compound of formula (IA) and the additional therapeutic agent. Alternatively, the combination therapy comprises administering to a subject the compound of formula (IA) and the additional therapeutic agent in a single composition.

The invention also refers to a combination of a compound of formula (I) and an additional therapeutic agent as defined above, for use in the prophylaxis and/or treatment of a hyperkinetic movement disorder. In a particular embodiment, the invention also refers to a combination of a compound of formula (IA) and an additional therapeutic agent as defined above, for use in the prophylaxis and/or treatment of a hyperkinetic movement disorder associated with Huntington's disease, Wilson's disease, Tourette syndrome, tardive dyskinesia and restless leg syndrome; particularly in the prophylaxis and/or treatment of a hyperkinetic movement disorder associated with Huntington's disease, Wilson's disease, Tourette syndrome, and restless leg syndrome.

In an embodiment of the invention the compound of formula (I) or pharmaceutically acceptable salts thereof can be conveniently administered to a patient. Thus, the compound for use of the present invention can be in form of a pharmaceutical composition comprising an effective amount of a compound of formula (I) or a pharmaceutically acceptable salt thereof, in combination with pharmaceutically acceptable excipients or carriers. This aspect can also be formulated as a pharmaceutical composition comprising an effective amount of a compound of formula (I) or a pharmaceutically acceptable salt thereof, in combination with pharmaceutically acceptable excipients or carriers for use in the prophylaxis and/or treatment of the hyperkinetic movement disorders.

In a particular embodiment of the invention, the compound of formula (IA) or pharmaceutically acceptable salts thereof can be conveniently administered to a patient. Thus, the compound for use of the present invention can be in form of a pharmaceutical composition comprising an effective amount of a compound of formula (IA) or a pharmaceutically acceptable salt thereof, in combination with pharmaceutically acceptable excipients or carriers. This aspect can also be formulated as a pharmaceutical composition comprising an effective amount of a compound of formula (IA) or a pharmaceutically acceptable salt thereof, in combination with pharmaceutically acceptable excipients or carriers for use in the prophylaxis and/or treatment of the hyperkinetic movement disorders associated with Huntington's disease, Wilson's disease, Tourette syndrome, tardive dyskinesia and restless leg syndrome; particularly in the prophylaxis and/or treatment of a hyperkinetic movement disorder associated with Huntington's disease, Wilson's disease, Tourette syndrome, and restless leg syndrome.

In an embodiment of the invention, the compound for use is in form of oral unit dosage form. In another embodiment of the invention, the compound for use is in form of intraoral unit dosage form including sublingual and buccal. Preferred pharmaceutical compositions are solid pharmaceutical compositions which rapidly disintegrate in the mouth of a subject, upon insertion into the buccal pouch or upon placement under the tongue. Examples of oral dosage forms suitable for the present invention include solid dosage forms like tablets, powders, capsules, sachets, as well as liquid syrups, suspensions and elixirs. Pharmaceutically acceptable carriers and excipients suitable for use in the oral formulations disclosed herein include, but are not limited to, diluents such as fillers and bulking agents, binders, lubricants, anticaking agents, disintegrants, sweeteners, buffering agents, preservatives, solubility enhancers, isotonic agents, suspending and dispersing agents, wetting or emulsifying agents, flavours and aromas, thickening agents, and vehicles.

In another embodiment, the compound for use of the present invention is in form of inhalation unit dosage form, which is inhaled through the mouth or the nose administered via an aerosol or a dry powder inhaler. Examples of inhalation dosage forms suitable for the present invention include, among others, solutions, suspensions, and powders. Solutions and suspensions can be administered by atomizers, nebulizers, and vaporizes aerosol devices; and powders can be administered by insufflators or puffers. Pharmaceutically acceptable carriers and excipients suitable for use in the inhalation formulations disclosed herein include, but are not limited to, preservatives, buffer salts, viscosity modifying agents, suspending agents, pH-adjusting agents, tonicity adjusting agent, solvent, co-solvent, surfactant and flavours.

The pressurized dispersers of the invention can be in form of a unit dose, bi-dose or multi-dose devices. The pressurized dispersers defined further comprise at least one propellant agent. The propellant is the agent that supplies the necessary pressure within the aerosol, nebulizer or insufflator system to expel the material from the container. Propellants are commonly classified as liquefied or compressed gases having vapour pressures generally exceeding atmospheric pressure. Examples of suitable propellants for the present invention includes hydrocarbons, especially halogenated derivatives of methane, ethane, and propane, low molecular weight hydrocarbons such as the butanes and pentanes, and compressed gases such as carbon dioxide, nitrogen, and nitrous oxide. Mixtures of propellants are frequently used to obtain desirable pressure, delivery, and spray characteristics.

In another embodiment, the compound for use of the present invention is in form of topical unit dosage form to be applied to the skin or mucous membranes of a patient to be treated. Examples of topical dosage forms suitable for the present invention include transdermal patches, transdermal plasters, solutions, aerosols and non-aerosol sprays, creams, powders, lotions, gels, ointments, pastes, emulsions, pens or sticks. Pharmaceutically acceptable carriers and excipients suitable for use in the topical formulations disclosed herein include, but are not limited to, an emollient, a thickener, a humectant, a pH-regulating agent, an antioxidant, a preservative agent, solubility enhancers, isotonic agents, suspending and dispersing agents, wetting or emulsifying agents, flavours and aromas, thickening agents, and vehicles or their mixtures.

Throughout the description and claims the term "comprise" and variations of the word, are not intended to exclude other technical features, additives, components, or steps. The term includes the expression "consist of" and variations thereof. Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

Example 1. VMAT2 Assay

VMAT2 Functional Assay determines the interaction between the compounds of the present invention and the VMAT2 present in isolated cerebral cortical vesicles. The VMAT2 assay used in the present invention is the assay disclosed by Sandoval et al in 2002 (Sandoval et al; "Methylphenidate redistributes vesicular monoamine transporter-2: role of dopamine receptors". *Journal of Neuroscience*. 2002, Vol. 22, pp. 8705-8710).

A. Materials
Transporter Source: Rat cortical vesicles
Buffers: 100 mM potassium tartrate, 1.7 mM ascorbic acid, 0.05 mM EGTA, 0.1 mM EDTA, 2 mM Magnesium-ATP and 25 mM HEPES.
RadioLigand:
Monoamine: [3H]-Dopamine
Final ligand concentration: 30 nM
KT (transport constant kinetic parameter of dopamine): 140 nM
Vmax (transport rate): 1800 fmol/mg tissue/min
B. Samples
Positive reference-control:
Reserpine
Concentration: 10 μM
Comparative sample: Tetrabenazine
Test Samples:
(IA) Bevantolol
(IB) Cinacalcet
(IC) Phenoxybenzamine
C. Method
(1) Rat cortical vesicles were purified using differential centrifugation, and the vesicles obtained were diluted in the assay buffer and pre-incubated with the positive-reference-control, the comparative sample or a compound of the invention for 30 minutes at room temperature.

(2) Uptake begins with the addition of [3H]-dopamine and the mixture is allowed to incubate for 15 minutes at room temperature.

(3) After that time, the reaction was stopped by vacuum filtration, and the amount of radioactivity of the radiolabeled [3H]-dopamine trapped onto the filters was determined.

(4) The radioactivity of the [3H]-dopamine trapped was determined using liquid scintillation spectrophotometry (Beckman and Perkin Elmer). The amount of radioactivity obtained with the comparative sample or a compound of the invention was compared with the amount of radioactivity obtained with the positive-reference control (reserpine).

D. Results

The half maximal inhibitory concentration (IC50) of the comparative sample and compounds of the invention was determined by measuring the concentration of competing ligand which displaced 50% of the specific binding of the [3H]-dopamine. The $IC_{50}$ value is converted to an absolute inhibition constant $K_i$ using the Cheng-Prusoff equation. Two separate independent experiments were performed.

The IC50 values were summarized in Table 1:

TABLE 1

| COMPOUND | IC50 (nM) | |
|---|---|---|
| | Experiment 1 | Experiment 2 |
| Comparative Sample (tetrabenazine) | 10.5 | 36.7 |
| Bevantolol (IA) | 42.8 | 63.0 |
| Cinacalcet (IB) | 44.6 | — |
| Phenoxybenzamine (IC) | 58.1 | — |

The IC50 values on Table 1 show that the compounds of the invention inhibit VMAT2 in the same order of magnitude than the comparative sample (tetrabenazine). The above-mentioned values of IC50 in the VMAT2 inhibition assay are good indicators of the efficacy of the treatment of hyperkinetic movement disorders by the compounds of the present invention.

REFERENCES CITED IN THE APPLICATION

1. WO2012117073
2. Sandoval et al; "Methylphenidate redistributes vesicular monoamine transporter-2: role of dopamine receptors". *Journal of Neuroscience.* 2002, Vol. 22, pp. 8705-8710.

The invention claimed is:

1. A method of treatment of a hyperkinetic movement disorder comprising the steps of:
administering a composition comprising a compound of formula (IA)

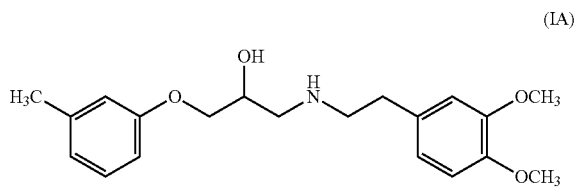 [SMILES: COc1ccc(CCNCC(O)COc2cccc(C)c2)cc1OC]

(IA)

or a pharmaceutically acceptable salt thereof for treatment of a hyperkinetic movement disorder to a subject in need thereof, wherein the hyperkinetic movement disorder is associated with a disease selected from a group consisting of Huntington's disease, Wilson's disease, Tourette syndrome, restless leg syndrome and tardive dyskinesia.

2. The method of claim 1, the compound of formula (IA) is administered as a single active ingredient.

3. The method of claim 1, further comprising the step of administering the compound of formula (IA) in a combination therapy with an additional therapeutic agent.

4. The method of claim 3, wherein the combination therapy comprises administering to a subject simultaneously, sequentially or separately the compound of formula (IA) and the additional therapeutic agent.

5. The method of claim 3, wherein the additional therapeutic agent is selected from the group consisting of a compound of formula (TB), a compound of formula (IC), a neuroleptic agent, an anti-glutamatergic agent, a dopamine depleting agent, an acetyl cholinesterase inhibitor, amantadine, riluzole, tetrabenazine, reserpine, and donepezil, and mixtures thereof wherein the compound of formula (TB) is

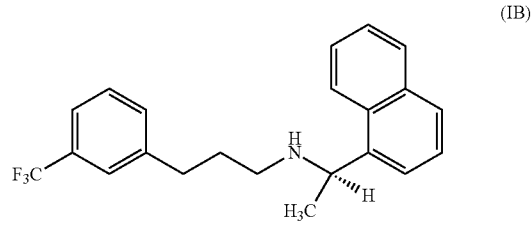 [SMILES: C[C@@H](NCCCc1cccc(C(F)(F)F)c1)c1cccc2ccccc12]

(IB)

and wherein the compound of formula (IC) is

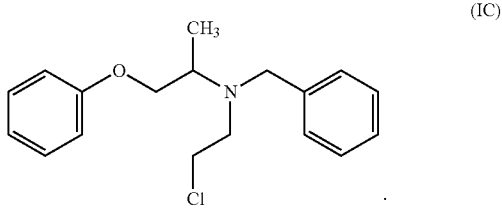 [SMILES: CC(COc1ccccc1)N(CCCl)Cc1ccccc1]

(IC)

6. The method of claim 1, wherein the hyperkinetic movement disorder is selected from the group consisting of abdominal dyskinesias, akathisic movements, asynergia, ataxia, athetosis, ballism, chorea, dysmetria, dystonia, hemifacial spasm, hyperekplexia, hypnogenic dyskinesias, jumpy stumps, moving toes and/or fingers, myoclonus, myokymia, myorhythmia, paroxysmal dyskinesias, tics, and tremors.

7. The method of claim 1, wherein the hyperkinetic movement disorder is chorea associated to Huntington's disease, Tourette syndrome, and tardive dyskinesia.

8. The method of claim 1, wherein the hyperkinetic movement disorder is chorea associated to Huntington's disease.

9. The method of claim 1, wherein the hyperkinetic movement disorder is tics associated to Tourette syndrome and tardive dyskinesia.

10. The method of claim 1, wherein the hyperkinetic movement disorder is ballism.

11. The method of claim 1, wherein the hyperkinetic movement disorder is dystonia.

12. The method of claim 1, wherein the composition comprises an effective amount of the compound of formula (IA) or a pharmaceutically acceptable salt thereof, in combination with pharmaceutically acceptable excipients or carriers.

13. The method of claim 12, wherein the pharmaceutical composition is in a dosage form selected from a group consisting of an oral unit dosage form, an intraoral unit dosage form, an inhalation dosage form, and a topical unit dosage form.

14. The method of claim 3, wherein the hyperkinetic movement disorder is chorea associated to Huntington's disease, Tourette syndrome, or tardive dyskinesia.

15. The method of claim 3, wherein the hyperkinetic movement disorder is chorea associated to Huntington's disease.

16. The method of claim 3, wherein the composition comprises an effective amount of the compound of formula (IA) or a pharmaceutically acceptable salt thereof, in combination with pharmaceutically acceptable excipients or carriers.

17. The method of claim 16, wherein the pharmaceutical composition is in a dosage form selected from a group consisting of an oral unit dosage form, an intraoral unit dosage form, an inhalation dosage form, and a topical unit dosage form.

\* \* \* \* \*